United States Patent
Fukino et al.

(10) Patent No.: US 10,853,414 B2
(45) Date of Patent: Dec. 1, 2020

(54) COMPUTER-IMPLEMENTED METHOD FOR PROVIDING CONTENT IN ACCORDANCE WITH EMOTIONAL STATE THAT USER IS TO REACH

(71) Applicant: Panasonic Intellectual Property Management Co., Ltd., Osaka (JP)

(72) Inventors: Miwa Fukino, Tokyo (JP); Motoji Ohmori, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 187 days.

(21) Appl. No.: 15/974,512

(22) Filed: May 8, 2018

(65) Prior Publication Data
US 2018/0336276 A1 Nov. 22, 2018

(30) Foreign Application Priority Data

May 17, 2017 (JP) ................................ 2017-097884

(51) Int. Cl.
*G06F 17/00* (2019.01)
*G06F 16/635* (2019.01)
(Continued)

(52) U.S. Cl.
CPC ............ *G06F 16/636* (2019.01); *A61B 5/165* (2013.01); *G06F 16/683* (2019.01); *A61B 5/02* (2013.01);
(Continued)

(58) Field of Classification Search
CPC ..... G06F 16/636; G06F 16/683; A61B 5/165; A61B 5/02; A61B 5/0205; A61B 5/02055; A61B 5/02405
See application file for complete search history.

(56) References Cited

U.S. PATENT DOCUMENTS 9,788,777 B1 * 10/2017 Knight .................. A61B 5/165
2008/0114219 A1 * 5/2008 Zhang .................. A61N 1/3621
600/301

(Continued)

FOREIGN PATENT DOCUMENTS

| JP | 2006-155157 | 6/2006 |
|---|---|---|
| JP | 2013-054447 A | 3/2013 |
| JP | 2016-002109 A | 1/2016 |

*Primary Examiner* — Tyler J Torgrimson
(74) *Attorney, Agent, or Firm* — Greenblum & Bernstein, P.L.C.

(57) ABSTRACT

A computer-implemented method receives, from a user device, user ID information, a target emotional state value, and target time information, acquires personal physiological rhythm data of a user including a plurality of emotional state values from a data storage, acquires present time information, determines a present emotional state value from the plurality of emotional state values, calculates a difference value between the present emotional state value and the target emotional state value, estimates a spontaneous variation of an emotional state value based on the physiological rhythm data, compensates the difference value by the spontaneous variation, selects a content that is expected to cause the emotional state value of the user to change by the compensated difference value, and provides the selected content to the user device.

12 Claims, 5 Drawing Sheets

(51) Int. Cl.
  *A61B 5/16* (2006.01)
  *G06F 16/683* (2019.01)
  *A61B 5/02* (2006.01)
  *A61B 5/024* (2006.01)
  *A61B 5/0205* (2006.01)

(52) U.S. Cl.
  CPC ......... *A61B 5/0205* (2013.01); *A61B 5/02055* (2013.01); *A61B 5/02405* (2013.01)

(56) References Cited

U.S. PATENT DOCUMENTS

| | | | | |
|---|---|---|---|---|
| 2008/0188354 A1* | 8/2008 | Pauws | ..................... | G10H 1/42 482/8 |
| 2009/0132593 A1* | 5/2009 | Lv | ..................... | G10H 1/0008 |
| 2010/0191037 A1* | 7/2010 | Cohen | ..................... | A61M 21/00 600/28 |
| 2011/0295843 A1* | 12/2011 | Ingrassia, Jr. | ....... | G06F 16/4387 707/723 |
| 2012/0117071 A1* | 5/2012 | Sakamoto | ............... | G06F 16/48 707/740 |
| 2012/0316660 A1* | 12/2012 | Luo | ..................... | G06F 16/78 700/94 |
| 2013/0297599 A1* | 11/2013 | Henshall | ............... | G11B 27/105 707/736 |
| 2014/0223462 A1* | 8/2014 | Aimone | ................. | G16H 40/67 725/10 |
| 2015/0199010 A1* | 7/2015 | Coleman | ............... | A61B 5/0006 345/156 |
| 2015/0206523 A1* | 7/2015 | Song | ..................... | G10H 7/002 84/609 |
| 2015/0297109 A1* | 10/2015 | Garten | ............... | A61B 5/04012 600/544 |
| 2016/0162565 A1* | 6/2016 | Jung | .................... | G06F 16/639 707/737 |
| 2016/0196105 A1* | 7/2016 | Vartakavi | ................ | G06F 3/165 700/94 |
| 2017/0339484 A1* | 11/2017 | Kim | ..................... | A61B 5/0478 |
| 2017/0352283 A1* | 12/2017 | Lau | ..................... | G09B 5/06 |
| 2019/0155840 A1* | 5/2019 | O'Konski | ............... | G06F 3/011 |
| 2019/0336724 A1* | 11/2019 | Li | ..................... | A61M 21/02 |

* cited by examiner

| USER ID | TIME ZONE | EMOTIONAL STATE VALUE ||
| | | AROUSAL DEGREE | EMOTIONAL VALENCE |
|---|---|---|---|
| 1111 | AM7-8 | -0.3 | -0.2 |
| | ... | ... | ... |
| | PM3-4 | +0.1 | -0.1 |
| | ... | ... | ... |
| | PM7-8 | +0.3 | +0.4 |

FIG. 4

| USER ID | TUNE ID | TUNE TITLE | FIRST MUSICAL FEATURE AMOUNT (TEMPO (BPM)) | SECOND MUSICAL FEATURE AMOUNT (AVERAGE SOUND GENERATION NUMBER) | THIRD MUSICAL FEATURE AMOUNT (BEAT INTENSITY 1) | EMOTIONAL STATE CHANGE VALUE | |
|---|---|---|---|---|---|---|---|
| | | | | | | AROUSAL DEGREE | EMOTIONAL VALENCE |
| 1111 | 0033 | A | 89.3 | 0.58 | 8.22 | +0.2 | +0.5 |
| | 0404 | B | 120.1 | 0.76 | 10.15 | +0.6 | −0.05 |
| | 7788 | C | 69.7 | 1.20 | 7.99 | +0.3 | +0.1 |

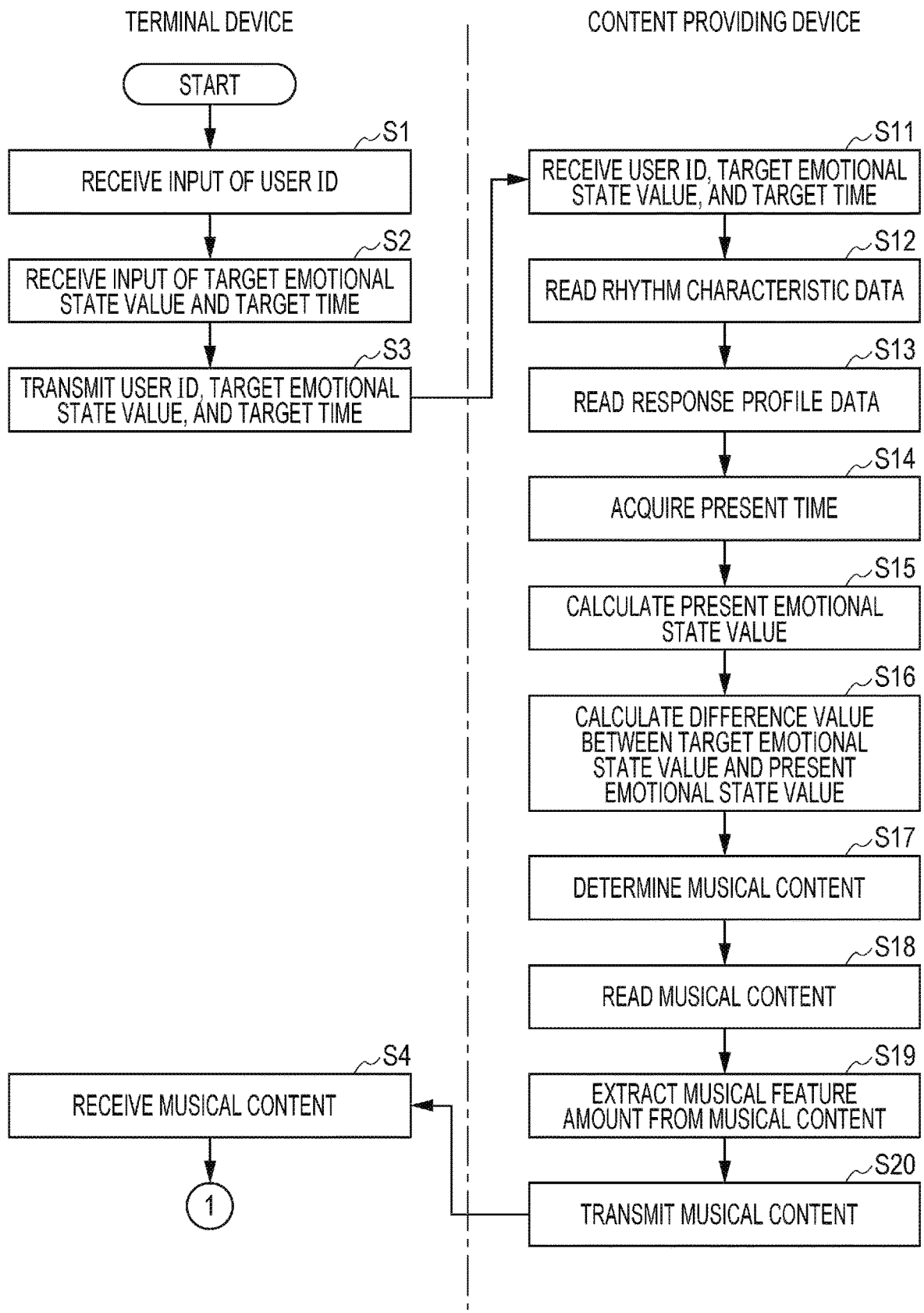

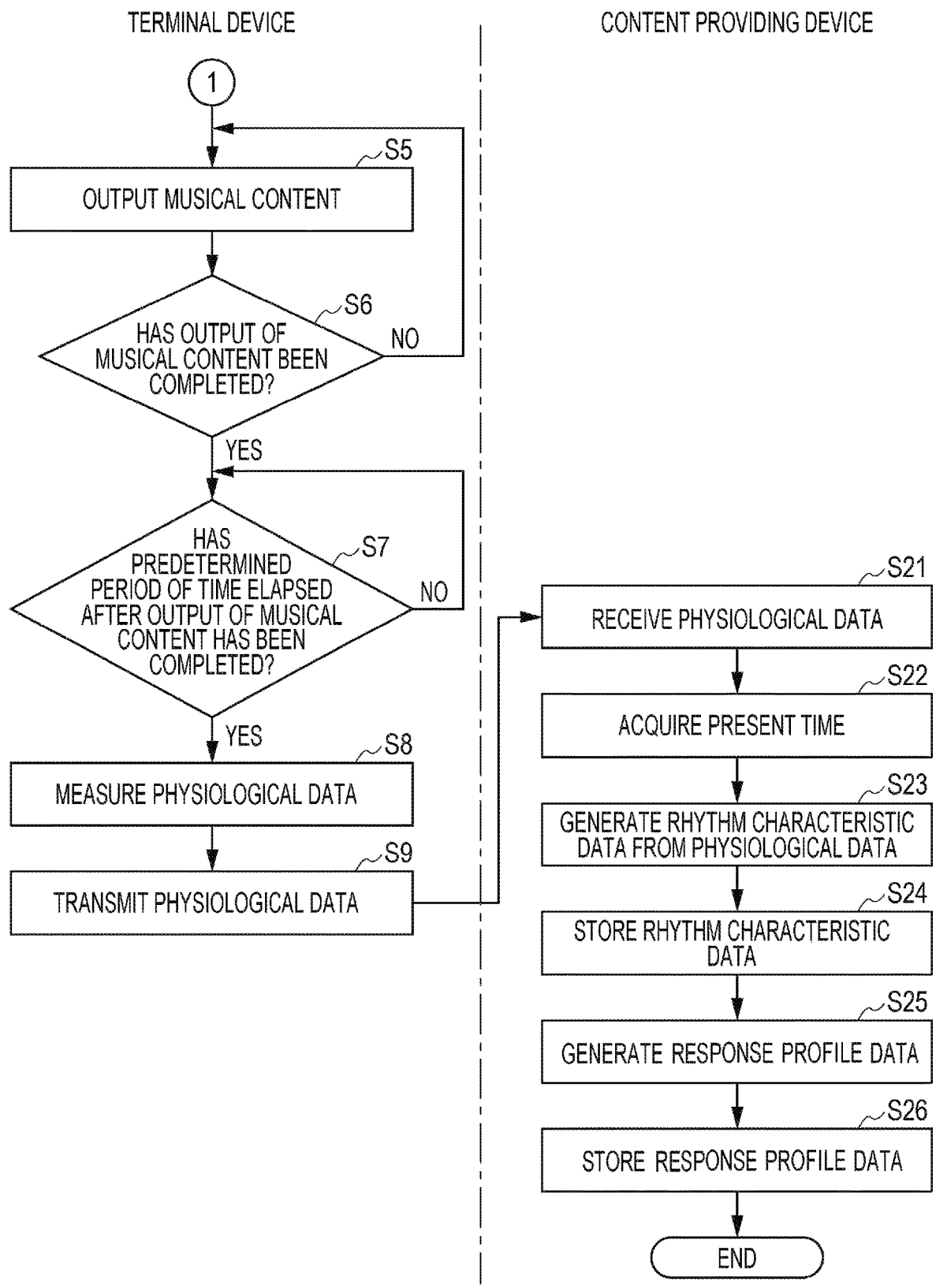

COMPUTER-IMPLEMENTED METHOD FOR PROVIDING CONTENT IN ACCORDANCE WITH EMOTIONAL STATE THAT USER IS TO REACH

BACKGROUND

1. Technical Field

The present disclosure relates to a content providing method, a content providing device, and a recording medium for providing a content for changing an emotional state to a user.

2. Description of the Related Art

Conventionally, techniques for analyzing emotions of a user to provide tunes suitable for the present emotion of the user have been present.

For example, Japanese Unexamined Patent Application Publication No. 2006-155157 discloses an automatic tune selecting device including a database for registering tune data of music and a musical sensitive space coordinate value which is the coordinate value of space expressing a mental impression of the tune, a voice inputter for detecting the user's voice, a voice analyzer for extracting a physical feature amount from a voice signal detected by the voice inputter, an emotional information generator for generating emotional information expressing the user's emotions based on the physical feature amount extracted by the voice analyzer, an emotional information/musical sensitive space coordinate converter for determining the musical sensitive space coordinate value which is the coordinate value of space expressing the mental impression of the recommended tune based on the emotional information obtained by the emotional information generator, a tune selector for selecting a tune closest to the musical sensitive space coordinate value determined by the emotional information/musical sensitive space coordinate converter, from the database, and a player for playing the tune selected by the tune selector. According to this automatic tune selecting device, a tune suitable for the present emotion of a user may be selected.

SUMMARY

In one general aspect, the techniques disclosed here feature a computer-implemented method for selectively providing content, the method including: receiving, from a user device, user ID information for specifying a user, a target emotional state value representing a target emotional state that the user is to reach, and target time information indicating a time when the user is to reach the target emotional state; acquiring personal physiological rhythm data of the user associated with the user ID information from a data storage, the personal physiological rhythm data including a plurality of emotional state values representing emotional states of the user at different times; acquiring present time information indicating a present time; determining one, which corresponds to the present time, selected from the plurality of emotional state values as a present emotional state value representing a present emotional state of the user; calculating a difference value between the present emotional state value and the target emotional state value; estimating, based on the physiological rhythm data, a spontaneous variation by which an emotional state value of the user is assumed to change during a period from the present time to the target time if no content is provided; compensating the difference value by the spontaneous variation; selecting, from among a plurality of contents registered in a content database, at least one content that is expected to cause the emotional state value of the user to change by the compensated difference value; and providing the selected at least one content to the user device.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 is a diagram illustrating an example of a response profile data stored in a response profile data storage in the present embodiment;

FIG. 5 is a first flowchart for explaining an operation of the content providing system in the present embodiment; and FIG. 6 is a second flowchart for explaining an operation of the content providing system in the present embodiment.

Figure 1:
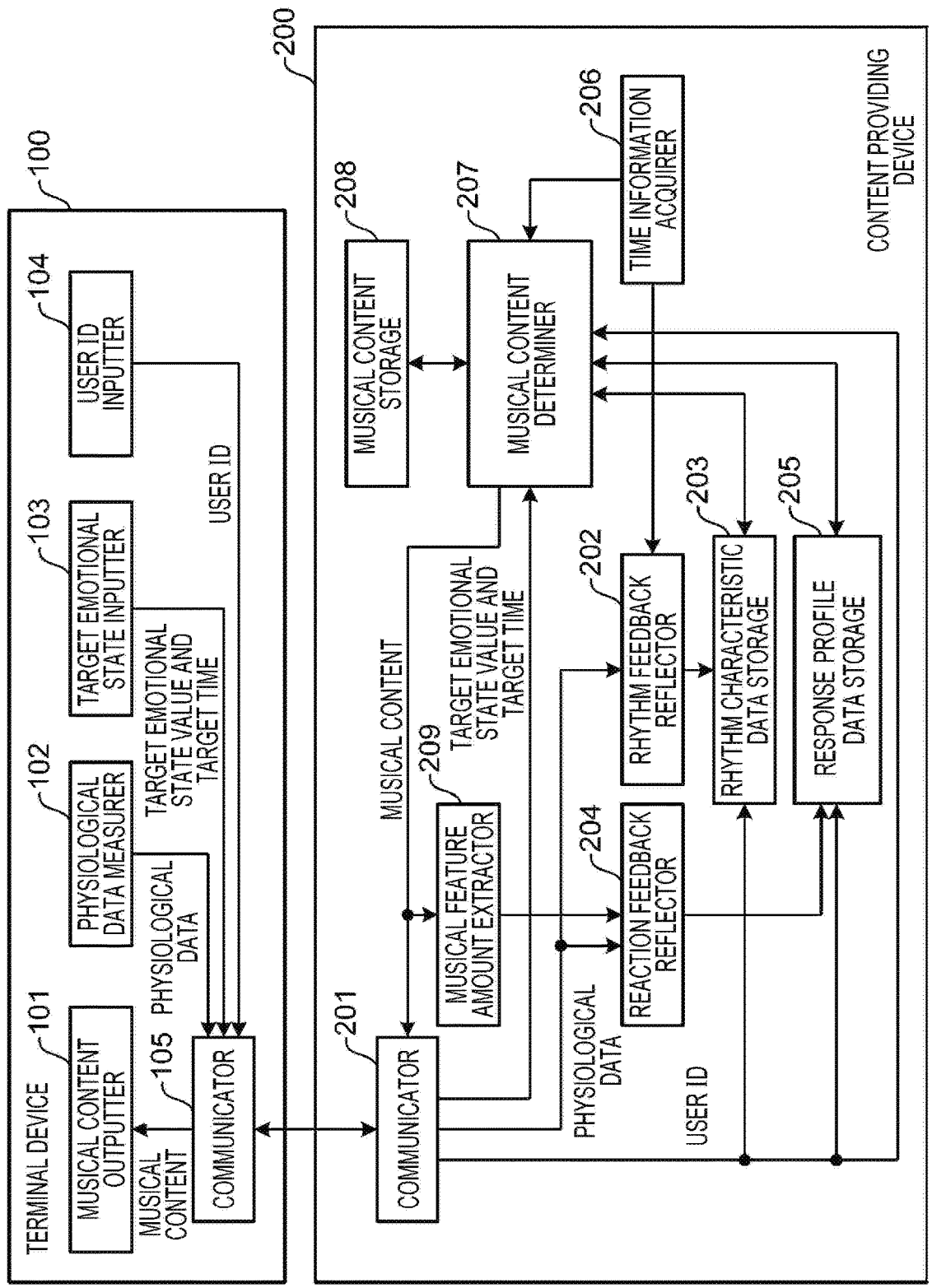
FIG. 1 is a block diagram of an example of a configuration of a content providing system according to an embodiment of the present disclosure.

DETAILED DESCRIPTION (Underlying Knowledge Forming Basis of the Present Disclosure)

A content providing method according to an aspect of the present disclosure acquires a target emotional state value representing an emotional state targeted by a user, acquires physiological data of the user, calculates a present emotional state value representing a present emotional state of the user based on the physiological data, calculates a difference value between the target emotional state value and the present emotional state value, determines a content for changing the emotional state in accordance with the difference value, and provides the determined content to the user.

With this configuration, a target emotional state value representing an emotional state targeted by a user is acquired. Physiological data of the user is acquired. A present emotional state value representing a present emotional state of the user is calculated based on the physiological data. A difference value between the target emotional state value and the present emotional state value is calculated. A content for changing the emotional state is determined in accordance with the difference value. The determined content is provided to the user.

Accordingly, in accordance with the difference value between the target emotional state value representing an emotional state targeted by the user and the present emotional state value representing the present emotional state of the user, the content for changing the emotional state is determined, and the determined content is provided to the user. This enables to guide the emotional state of the user to the emotional state targeted by the user.

Furthermore, in the above-described content providing method, user specification information for specifying the user may be acquired. The physiological data of the user may be acquired when a predetermined period of time has elapsed after the content has been provided. A feature amount may be extracted from the provided content. Based on the acquired physiological data and the feature amount, an emotional state change value representing an emotional state of the user that has been changed by the provided content may be calculated. The user specification information, content specification information for specifying the content, and the emotional state change value may be stored in an emotional state change value storage in association with each other. The content specification information corresponding to the emotional state change value approximate to the difference value may be read from the emotional state change value storage. A content corresponding to the content specification information may be read from a content storage.

With this configuration, user specification information for specifying the user is acquired. The physiological data of the user is acquired when a predetermined period of time has elapsed after the content has been provided. A feature amount is extracted from the provided content. Based on the acquired physiological data and the feature amount, an emotional state change value representing an emotional state of the user that has been changed by the provided content is calculated. The user specification information, content specification information for specifying the content, and the emotional state change value are stored in an emotional state change value storage in association with each other. The content specification information corresponding to the emotional state change value approximate to the difference value is read from the emotional state change value storage. A content corresponding to the content specification information is read from a content storage.

Even when the same content is provided, the change in the emotional state may be different depending on the user. For this reason, the emotional state change value representing an emotional state of the user that has been changed by the provided content is calculated, and the user specification information, the content specification information for specifying the content, and the calculated emotional state change value are stored in the emotional state change value storage in association with each other. This enables to store the emotional state change value in accordance with each individual user and thus provide a content in accordance with the each individual user.

Furthermore, in the above-described content providing method, the content may include a plurality of contents. A target time indicating a time for reaching the target emotional state value, which is targeted by the user, may be acquired. When the emotional state change value is smaller than the difference value, a plurality of pieces of content specification information for specifying the plurality of contents may be read from the emotional state change value storage such that the total value of the emotional state change values for the plurality of contents becomes equal to the difference value before the target time is reached.

With this configuration, a content includes a plurality of contents. A target time indicating a time for reaching the target emotional state value, which is targeted by the user, is acquired. When the emotional state change value is smaller than the difference value, a plurality of pieces of content specification information for specifying the plurality of contents are read from the emotional state change value storage such that the total value of the emotional state change values for the plurality of contents becomes equal to the difference value before the target time is reached.

Accordingly, by providing a plurality of contents to the user such that the total value of the emotional state change values for the plurality of contents becomes equal to the difference value before the target time is reached, the emotional state of the user can be guided to the emotional state targeted by the user.

Furthermore, in the above-described content providing method, a change pattern of the emotional state value of the user that cyclically changes in a predetermined period may be acquired. Based on the change pattern, the emotional state value changing from the present time to the target time may be calculated as a compensated value. The calculated compensated value may be used to compensate the difference value.

With this configuration, a change pattern of the emotional state value of the user that cyclically changes in a predetermined period is acquired. Based on the change pattern, the emotional state value changing from the present time to the target time is calculated as a compensated value. The calculated compensated value is used to compensate the difference value.

Accordingly, in a state in which no content is provided, the difference value is calculated with consideration for the emotional state value changing from the present time to the target time, whereby the content can be determined.

Furthermore, in the above-described content providing method, the content may include a musical content that changes the emotional state.

With this configuration, because the content includes a musical content that changes the emotional state, the emotional state of the user can be guided to the emotional state targeted by the user by letting the user listen to the musical content.

Furthermore, in the above-described content providing method, the content may include a video content that changes the emotional state.

With this configuration, because the content includes a video content that changes the emotional state, the emotional state of the user can be guided to the emotional state targeted by the user by letting the user watch the video content.

Furthermore, in the above-described content providing method, the content may include a light content that changes the emotional state by changing the color of the light in the space in which the user is located.

With this configuration, because the content includes a light content that changes the emotional state by changing the color of the light in the space in which the user is located, the emotional state of the user can be guided to the emotional state targeted by the user by letting the user see the light content.

Furthermore, in the above-described content providing method, the target emotional state value and the present emotional state value may be represented by two-dimensional coordinates indicating arousal degree and emotional valence.

With this configuration, because the target emotional state value and the present emotional state value are represented by two-dimensional coordinates indicating arousal degree and emotional valence, the emotional state of the user can be represented by two values of arousal degree and emotional valence.

Furthermore, in the above-described content providing method, the two-dimensional coordinates may be displayed. On the displayed two-dimensional coordinates, an input of the target emotional state value by the user may be received.

With this configuration, because the two-dimensional coordinates are displayed and on the displayed two-dimensional coordinates, an input of the target emotional state value by the user is received, the user can easily input the target emotional state value.

Furthermore, in the above-described content providing method, the physiological data may include at least one of the user's blood flow, heart rate, pulse rate, brain wave, and blood pressure.

With this configuration, because the physiological data includes at least one of the user's blood flow, heart rate, pulse rate, brain wave, and blood pressure, the present emotional state of the user can be estimated based on the at least one of the user's blood flow, heart rate, pulse rate, brain wave, and blood pressure.

A content providing device according to another aspect of the present disclosure includes a target emotional state value acquirer that acquires a target emotional state value representing an emotional state targeted by a user, a physiological data acquirer that acquires physiological data of the user, a present emotional state value calculator that calculates a present emotional state value representing a present emotional state of the user based on the physiological data, a difference value calculator that calculates a difference value between the target emotional state value and the present emotional state value, a content determiner that determines a content for changing the emotional state in accordance with the difference value, and a content provider that provides the determined content to the user.

With this configuration, a target emotional state value representing an emotional state targeted by a user is acquired. Physiological data of the user is acquired. A present emotional state value representing a present emotional state of the user is calculated based on the physiological data. A difference value between the target emotional state value and the present emotional state value is calculated. A content for changing the emotional state is determined in accordance with the difference value. The determined content is provided to the user.

Accordingly, in accordance with the difference value between the target emotional state value representing an emotional state targeted by the user and the present emotional state value representing the present emotional state of the user, the content for changing the emotional state is determined, and the determined content is provided to the user. This enables to guide the emotional state of the user to the emotional state targeted by the user.

A content providing program according to another aspect of the present disclosure causes a computer to function as a target emotional state value acquirer that acquires a target emotional state value representing an emotional state targeted by a user, a physiological data acquirer that acquires physiological data of the user, a present emotional state value calculator that calculates a present emotional state value representing a present emotional state of the user based on the physiological data, a difference value calculator that calculates a difference value between the target emotional state value and the present emotional state value, and a content determiner that determines a content for changing the emotional state in accordance with the difference value.

With this configuration, a target emotional state value representing an emotional state targeted by a user is acquired. Physiological data of the user is acquired. A present emotional state value representing a present emotional state of the user is calculated based on the physiological data. A difference value between the target emotional state value and the present emotional state value is calculated. A content for changing the emotional state is determined in accordance with the difference value.

Accordingly, in accordance with the difference value between the target emotional state value representing an emotional state targeted by the user and the present emotional state value representing the present emotional state of the user, the content for changing the emotional state is determined. This enables to guide the emotional state of the user to the emotional state targeted by the user.

It is to be noted that in the present disclosure, all or a part of the functions of the device may be implemented as a computer program executed by a computer including a processor, a memory, and the like. In such a case, the computer program may be recorded in a computer-readable non-transitory recording medium such as a CD-ROM.

An embodiment of the present disclosure will be described below with reference to the attached drawings. It is to be noted that the embodiment described below is an example embodying the present disclosure and is not intended to limit the technical scope of the present disclosure.

Embodiment

FIG. 1 is a block diagram of an example of a configuration of a content providing system according to an embodiment of the present disclosure. The content providing system illustrated in FIG. 1 includes a terminal device 100 and a content providing device 200.

The terminal device 100 is a personal computer, a tablet type computer, or a smartphone, for example, and is arranged in a space in which a user is located.

The content providing device 200 is a server including a processor, memory, and the like, for example, and provides a content for changing an emotional state of the user. It is to be noted that in the present embodiment, although the content providing device 200 provides a musical content as an example of the content to the user, the present disclosure is not particularly limited to this. The content providing device 200 may provide a video content for changing an emotional state of the user and may provide a light content for changing an emotional state of the user by changing the color of the light in the space in which the user is located. The terminal device 100 and the content providing device 200 are communicably connected to each other via a network such as the Internet.

The terminal device 100 includes a musical content outputter 101, a physiological data measurer 102, a target emotional state inputter 103, a user ID inputter 104, and a communicator 105.

The musical content outputter 101 is a speaker, for example, and outputs a musical content received by the communicator 105 to the outside. It is to be noted that the musical content outputter 101 may not be incorporated into the terminal device 100, or may be located outside the terminal device 100.

The physiological data measurer 102 includes various sensors, for example, and measures physiological data of the user and acquires the measured data. Furthermore, the physiological data measurer 102 measures physiological data of the user at the time when a predetermined period of time has elapsed after the musical content is provided and acquires the measured data. To the physiological data, the user's blood flow, heart rate, pulse rate, brain wave, blood pressure, physiological gas, respiration, and/or body temperature correspond, for example. The physiological data measurer 102 includes a sensor that uses a high-sensitive spectrum diffusion type millimeter-wave radar and the like to measure the user's pulse wave in a noncontact manner, for example, and detects the user's heart rate and heart rate variability.

It is to be noted that the configuration of the physiological data measurer 102 is not particularly limited to this example. A smartwatch for measuring data such as physiological data of a person may be attached to the user and the data such as physiological data may be acquired from the smartwatch. In such a case, the terminal device 100 includes a physiological data acquirer that acquires the measured physiological data.

The target emotional state inputter 103 is a keyboard, a mouse, or a touch panel display, for example, and receives an input of a target emotional state value representing an emotional state targeted by a user. Furthermore, the target emotional state inputter 103 receives an input of a target time indicating a time for reaching the target emotional state value, which is targeted by the user.

Figures 2, 3:
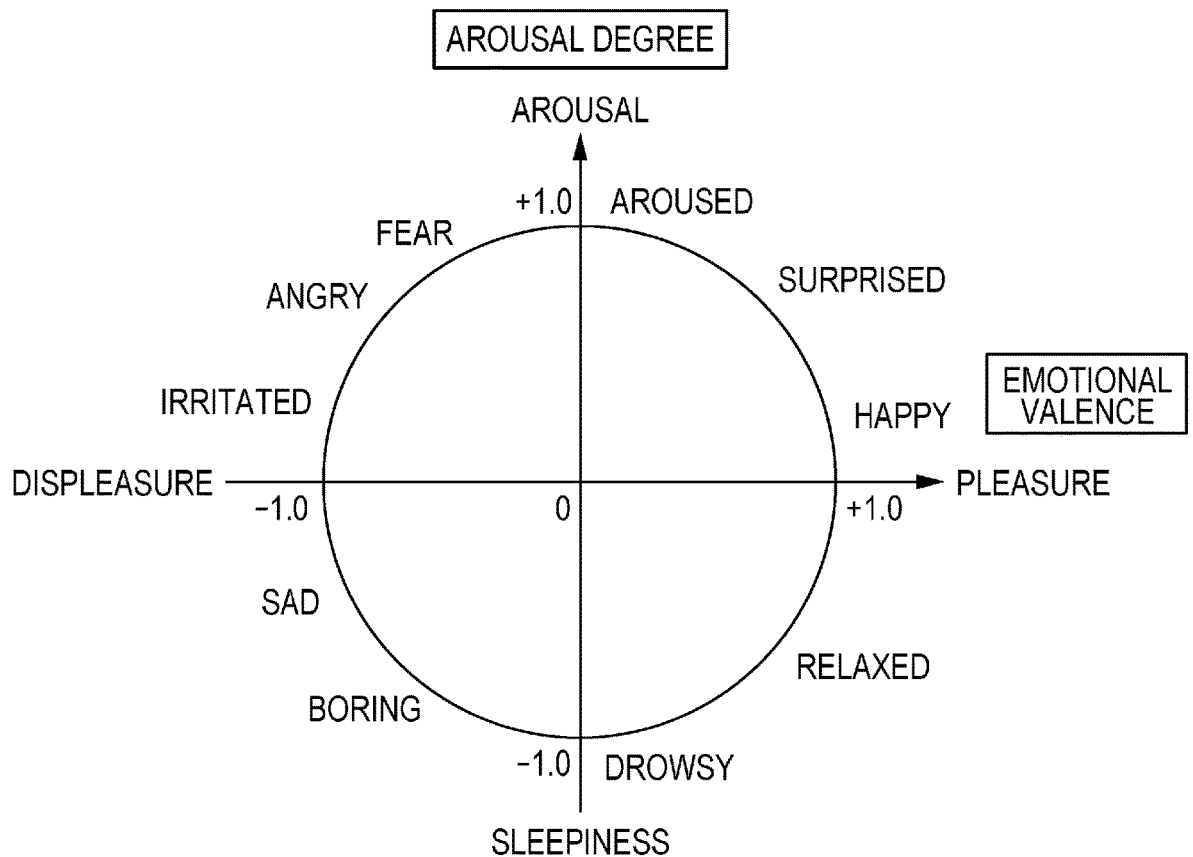
FIG. 2 is a diagram explaining a target emotional state value input by a target emotional state inputter in the present embodiment.
FIG. 3 is a diagram illustrating an example of rhythm characteristic data stored in a rhythm characteristic data storage in the present embodiment.

FIG. 2 is a diagram explaining a target emotional state value input by a target emotional state inputter in the present embodiment. In FIG. 2, the vertical axis represents arousal degree and the horizontal axis represents emotional valence.

The target emotional state value is represented by two-dimensional coordinates indicating arousal degree and emotional valence. The target emotional state inputter 103 displays the two-dimensional coordinates and receives an input of the target emotional state value by the user on the displayed two-dimensional coordinates. The two-dimensional coordinates illustrated in FIG. 2 are based on a circumplex model of affect of Russell (James A. Russell, "A Circumplex Model of Affect", Journal of Personality and Social Psychology, 1980, Vol. 39, No. 6, 1161-1178).

Arousal degree is represented by a value from −1.0 (sleepiness) to +1.0 (arousal), and emotional valence is represented by a value from −1.0 (displeasure) to +1.0 (pleasure). The user selects a desired position in the circumplex model of affect in accordance with the emotional state targeted by the user.

The user ID inputter 104 is a keyboard, a mouse, or a touch panel display, for example, and receives an input of a user ID (user specification information) for specifying the user. It is to be noted that the user ID inputter 104 may be a physiological authentication device that authenticates the user with physiological information such as a fingerprint or a card reader that authenticates the user with an IC card.

The communicator 105 transmits the target emotional state value and the target time input by the target emotional state inputter 103 to the content providing device 200. Furthermore, the communicator 105 transmits the user ID input by the user ID inputter 104 to the content providing device 200. Furthermore, the communicator 105 transmits the physiological data measured by the physiological data measurer 102 to the content providing device 200. Furthermore, the communicator 105 receives the musical content transmitted from the content providing device 200.

It is to be noted that the communicator 105 may transmit the target emotional state value, the user ID, and the target time separately and may transmit the target emotional state value, the user ID, and the target time collectively.

The content providing device 200 includes a communicator 201 a rhythm feedback reflector 202, a rhythm characteristic data storage 203, a reaction feedback reflector 204, a response profile data storage 205, a time information acquirer 206, a musical content determiner 207, a musical content storage 208, and a musical feature amount extractor 209.

The communicator 201 receives the target emotional state value, the user ID, and the target time transmitted from the terminal device 100. Furthermore, the communicator 201 receives the physiological data transmitted from the terminal device 100. That is to say, the communicator 201 acquires the physiological data while acquiring the target emotional state value. Furthermore, the communicator 201 transmits the musical content determined by the musical content determiner 207 to the terminal device 100. The communicator 201 outputs the received target emotional state value to the musical content determiner 207. The communicator 201 outputs the received user ID to the musical content determiner 207, the rhythm characteristic data storage 203, and the response profile data storage 205. The communicator 201 outputs the received physiological data to the rhythm feedback reflector 202 and the reaction feedback reflector 204.

The time information acquirer 206 acquires time information indicating the present time. The time information acquirer 206 outputs the time information to the musical content determiner 207 and the rhythm feedback reflector 202.

The rhythm feedback reflector 202 calculates the present emotional state value representing the present emotional state of the user based on the physiological data. The rhythm feedback reflector 202 calculates an emotional state value at the present time based on the time information input from the time information acquirer 206 and the physiological data received by the communicator 201. The rhythm feedback reflector 202 stores therein in advance a table associating the physiological data value and the emotional state value or a function for converting the physiological data value into the emotional state value, for example. The rhythm feedback reflector 202 reads the emotional state value associated with the received physiological data value from the table or calculates the emotional state value by substituting the received physiological data value with the function. The rhythm feedback reflector 202 stores rhythm characteristic data associating the present time and the emotional state value in the rhythm characteristic data storage 203. The rhythm characteristic data indicates a periodic emotional change pattern depending on the time zone for each user.

The rhythm characteristic data storage 203 stores therein the rhythm characteristic data associating the user ID received by the communicator 201 and the time and the emotional state value calculated by the rhythm feedback reflector 202.

FIG. 3 is a diagram illustrating an example of the rhythm characteristic data stored in the rhythm characteristic data storage in the present embodiment.

As illustrated in FIG. 3, the rhythm characteristic data includes the user ID, the time zone, and the emotional state value. The rhythm characteristic data includes the emotional state value per hour, for example, and includes the emotional state value in a predetermined period, for example, one day, one week, or one month. In FIG. 3, the user ID is "1111", for example, and the emotional state values (arousal degree, emotional valence) being (−0.3, −0.2) are associated with the time zone from 7:00 AM to 8:00 AM. It is to be noted that the emotional state values may be average values of the emotional state values in the predetermined time zone, or may be the emotional state values at an optional time within the predetermined time zone. Furthermore, the rhythm characteristic data storage 203 may store therein in advance general emotional state values of a person as initial values of the rhythm characteristic data. The initial values may be updated by the rhythm feedback reflector 202.

For example, the rhythm feedback reflector 202 may acquire the physiological data of the user in one day, convert the acquired physiological data in one day into the emotional state values, and store the emotional state values in one day in the rhythm characteristic data storage 203. It is to be noted that the rhythm feedback reflector 202 preferably converts the physiological data acquired in a state in which no musical content is provided to the user into the emotional state values and stores a change pattern of the emotional state values in one day in the rhythm characteristic data storage 203 as the rhythm characteristic data.

The musical feature amount extractor 209 extracts a predetermined musical feature amount from the provided musical content. The musical feature amount extractor 209 extracts a physical feature amount of a musical signal. As physical feature amounts, for example, tempo (speed of a tune), whiteness of beat (appearance frequency ratio between a sound contributing and a sound not contributing to beat formation), spectrum variation degree (degree of spectrum variation between frames having a predetermined duration), average sound generation number (sound generation frequency of a sound generated in the tune), sound generation non-periodicity (degree of non-periodicity of a sound generated in the tune), beat period (duration corresponding to a quarter note in the tune), beat period ratio (period ratio between a sound corresponding to a quarter note in the tune and a sound dominantly generated), beat intensity 1 (intensity of a sound generated in a period corresponding to approximately half the beat period), beat intensity 2 (intensity of a sound generated in a period corresponding to approximately quarter the beat period), beat intensity ratio (ratio between the beat intensity 1 and the beat intensity 2), and the like are extracted. It is to be noted that the musical feature amount extractor 209 extracts at least one type of musical feature amount out of a plurality of types of musical feature amounts.

The reaction feedback reflector 204 calculates the emotional state change value representing the emotional state of the user that has been changed with the musical content provided, based on the physiological data of the user at the time when a predetermined period of time has elapsed after the musical content is provided, which has been received by the communicator 201, and the musical feature amount extracted by the musical feature amount extractor 209. The reaction feedback reflector 204 stores response profile data associating the user ID, a tune ID for specifying the musical content (content specification information), a tune title indicating the title of the musical content, the musical feature amount, and the calculated emotional state change value in the response profile data storage 205. The response profile data include information on a personal response profile to music, for example.

The response profile data storage 205 stores therein response profile data associating the user ID, the tune ID, the tune title, the musical feature amount, and the emotional state change value.

FIG. 4 is a diagram illustrating an example of a response profile data stored in a response profile data storage in the present embodiment.

As illustrated in FIG. 4, the response profile data includes the user ID, the tune ID, the tune title, the musical feature amount, and the emotional state change value. The musical feature amount includes a first musical feature amount, a second musical feature amount, and a third musical feature amount. The first musical feature amount is the tempo, the second musical feature amount is the average sound generation number, and the third musical feature amount is the beat intensity 1. It is to be noted that in the present embodiment, the number of the musical feature amounts associated with one musical content is not limited to three. In FIG. 4, the user ID is "1111", the tune ID is "0033", the tune title is "A", the first musical feature amount (tempo) is "89.3 BPM", the second musical feature amount (average sound generation number) is "0.58", the third musical feature amount (the beat intensity 1) is "8.22", and the emotional state change values (arousal degree, emotional valence) are (+0.2, +0.5), for example.

The emotional state change value represents the emotional state changed with the user listening to the musical content. That is to say, in the example in FIG. 4, the user whose user ID is "1111" listens to the musical content whose tune ID is "0033", whereby the arousal degree increases by +0.2 and the emotional valence increases by +0.5.

The musical content storage 208 stores therein a plurality of musical contents. The musical content storage 208 stores therein the tune ID, the tune title, and the musical content in association with each other.

The musical content determiner 207 acquires the target emotional state value, the target time, and the user ID that have been received by the communicator 201. The musical content determiner 207 calculates the difference value between the target emotional state value and the present emotional state value and determines the musical content for changing the emotional state in accordance with the calculated difference value. The musical content determiner 207 acquires the present time from the time information acquirer 206 and reads the emotional state value corresponding to the present time from the rhythm characteristic data stored in the rhythm characteristic data storage 203 and corresponding to the acquired user ID as the present emotional state value.

The musical content determiner 207 extracts the tune ID corresponding to the emotional state change value approximate to the difference value from the response profile data stored in the response profile data storage 205 and corresponding to the acquired user ID and reads the musical content corresponding to the extracted tune ID from the musical content storage 208.

Furthermore, the musical content determiner 207 compensates the difference value between the target emotional state value and the present emotional state value based on the rhythm characteristic data corresponding to the user ID. That is to say, the musical content determiner 207 acquires the rhythm characteristic data indicating the change pattern of the emotional state values of the user that cyclically changes in a predetermined period. The musical content determiner 207 calculates the emotional state value changing from the present time to the target time as the compensated value based on the rhythm characteristic data and compensates the difference value using the calculated compensated value. The musical content determiner 207 calculates, as the compensated value, the emotional state value automatically changing from the present time to the target time if no tune is played, from the rhythm characteristic data.

Specifically, the musical content determiner 207 reads the emotional state value in the time zone corresponding to the present time and the emotional state value in the time zone corresponding to the target time from the rhythm characteristic data, subtracts the emotional state value in the time zone corresponding to the present time from the emotional state value in the time zone corresponding to the target time, and calculates the subtracted value as the compensated value. The musical content determiner 207 then compensates the difference value by subtracting the compensated value from the difference value between the target emotional state value and the present emotional state value.

Furthermore, when the emotional state change value is smaller than the difference value, the musical content determiner 207 may read a plurality of tune IDs for specifying a plurality of musical contents from the response profile data storage 205 such that the total value of the emotional state change values for the plurality of contents becomes equal to the difference value before the target time is reached. For example, when the difference values (arousal degree, emotional valence) are (+1.2, +0.9), the unit time of compensation for compensating the emotional state of the user with one musical content is 10 minutes, and the period from the present time to the target time is one hour, the musical content determiner 207 selects a musical content whose emotional state change values (arousal degree, emotional valence) are (+0.2, +0.15) six times. The terminal device 100 plays the musical content six times and thereby changes the emotional state of the user to be the target emotional state value before the target time. Furthermore, when the difference values (arousal degree, emotional valence) are (+1.2, +0.9), the unit time of compensation for compensating the emotional state of the user with one musical content is 10 minutes, and the period from the present time to the target time is two hour, the musical content determiner 207 selects a musical content whose emotional state change values (arousal degree, emotional valence) are (+0.1, +0.075) twelve times.

The musical content determiner 207 outputs the determined musical content to the communicator 201. The communicator 201 transmits the musical content determined by the musical content determiner 207 to the terminal device 100. The communicator 105 of the terminal device 100 receives the musical content transmitted by the content providing device 200 and outputs the received musical content to the musical content outputter 101. The musical content outputter 101 outputs the musical content received by the communicator 105 and provides the determined musical content to the user.

At this point, the communicator 201 corresponds to an example of the target emotional state value acquirer and the physiological data acquirer. The rhythm feedback reflector 202 corresponds to an example of the present emotional state value calculator. The musical content determiner 207 corresponds to an example of the difference value calculator and the content determiner. The musical content outputter 101 corresponds to an example of the content provider.

Next, an operation of the content providing system in the present embodiment will be described.

FIG. 5 is a first flowchart for explaining an operation of the content providing system in the present embodiment. FIG. 6 is a second flowchart for explaining an operation of the content providing system in the present embodiment.

Firstly, at Step S1, the user ID inputter 104 of the terminal device 100 receives an input of the user ID by the user.

Next, at Step S2, the target emotional state inputter 103 receives an input of the target emotional state value and the target time by the user. For example, the target emotional state inputter 103 receives an input of the target emotional state value by receiving selection of coordinate values targeted by the user on the circumplex model of affect illustrated in FIG. 2. Furthermore, the target emotional state inputter 103 may receive an input by the user of the target time indicating the time taken from the present time to the time targeted by the user.

Next, at Step S3, the communicator 105 transmits the user ID input by the user ID inputter 104 and the target emotional state value and target time that have been input by the target emotional state inputter 103 to the content providing device 200.

Next, at Step S11, the communicator 201 of the content providing device 200 receives the user ID, the target emotional state value, and the target time that have been transmitted by the terminal device 100.

Next, at Step S12, the musical content determiner 207 reads the rhythm characteristic data corresponding to the received user ID from the rhythm characteristic data storage 203.

Next, at Step S13, the musical content determiner 207 reads the response profile data corresponding to the received user ID from the response profile data storage 205.

Next, at Step S14, the time information acquirer 206 acquires the time information indicating the present time. The time information acquirer 206 outputs the acquired time information to the musical content determiner 207.

Next, at Step S15, the musical content determiner 207 calculates the present emotional state value corresponding to the present time based on the rhythm characteristic data read from the rhythm characteristic data storage 203 and the present time acquired by the time information acquirer 206. For example, when the rhythm characteristic data includes the emotional state values in one day, the musical content determiner 207 extracts the emotional state value corresponding to the present time from the rhythm characteristic data.

Next, at Step S16, the musical content determiner 207 calculates the difference value between the received target emotional state value and the calculated present emotional state value. For example, when the target emotional state values (arousal degree, emotional valence) are (+0.8, +0.4) and the present emotional state values (arousal degree, emotional valence) are (−0.3, −0.2), the difference values (arousal degree, emotional valence) are (+1.1, +0.6).

At this point, the musical content determiner 207 compensates the difference value between the target emotional state value and the present emotional state value based on the rhythm characteristic data corresponding to the user ID. For example, the present time is 3:00 PM and the target time is 7:00 PM, with the rhythm characteristic data illustrated in FIG. 3, the emotional state values (arousal degree, emotional valence) at 3:00 PM are (+0.1, −0.1) and the emotional state values (arousal degree, emotional valence) at 7:00 PM are (+0.3, +0.4). The rhythm characteristic data indicates a periodic emotional change pattern depending on the time zone, and thus, even if the user does not listen to the music, the emotional state value of arousal degree increases by +0.2 and the emotional state value of emotional valence increases by +0.5 when the time reaches 7:00 PM from 3:00 PM.

The musical content determiner 207 thus reads the emotional state value in the time zone corresponding to the present time and the emotional state value in the time zone corresponding to the target time from the rhythm characteristic data, subtracts the emotional state value in the time zone corresponding to the present time from the emotional state value in the time zone corresponding to the target time, and calculates the subtracted value as the compensated value. This compensated value is the emotional state value automatically changing even if no tune is played at the target time. In the above-described example, the compensated values (arousal degree, emotional valence) are (+0.2, +0.5). When the difference values (arousal degree, emotional valence) between the target emotional state values and the present emotional state values are (+1.1, +0.6), the musical content determiner 207 calculates the subtracted values (+0.9, +0.1) obtained by subtracting the compensated values from the difference values as the difference values after compensation.

Next, at Step S17, the musical content determiner 207 extracts the tune ID corresponding to the emotional state change value approximate to the difference value from the read response profile data and reads the musical content corresponding to the extracted tune ID from the musical content storage 208. At this point, when the emotional state change value approximate to the difference value is not present relative to the response profile data and each of a plurality of emotional state change values corresponding to a plurality of musical contents included in the response profile data is smaller than the difference value, the musical content determiner 207 may select a plurality of musical contents with which the total value of the emotional state change values becomes equal to the difference value before the received target time is reached and extract a plurality of tune IDs corresponding to the selected plurality of musical contents from the response profile data. Furthermore, the plurality of musical contents to be selected may be the same musical contents, or may be different musical contents. The same musical contents may be played for a plurality of times, and each of the different musical contents may be played.

Next, at Step S18, the musical content determiner 207 reads the determined musical content from the musical content storage 208. The musical content determiner 207 reads the musical content corresponding to the tune ID that has been extracted from the response profile data from the musical content storage 208. At this point, when a plurality of musical contents have been determined, the musical content determiner 207 may read the determined plurality of musical contents. The musical content determiner 207 outputs the read musical contents to the communicator 201.

Next, at Step S19, the musical feature amount extractor 209 extracts a predetermined musical feature amount from the musical content output from the musical content determiner 207.

Next, at Step S20, the communicator 201 transmits the read musical content by the musical content determiner 207 to the terminal device 100. At this point, when a plurality of musical contents have been determined, the communicator 201 may transmit the determined plurality of musical contents to the terminal device 100.

Next, at Step S4, the communicator 105 of the terminal device 100 receives the musical content transmitted by the content providing device 200. At this point, when a plurality of musical contents have been transmitted by the content providing device 200, the communicator 105 may receive the plurality of musical contents. The communicator 105 outputs the received musical contents to the musical content outputter 101.

Next, at Step S5, the musical content outputter 101 outputs the musical contents received by the communicator 105 to the outside. At this point, when a plurality of musical contents have been received by the communicator 105, the musical content outputter 101 outputs the plurality of musical contents sequentially to the outside. Furthermore, when a plurality of musical contents are output, the musical content outputter 101 outputs a first musical content and a second musical content sequentially out of the plurality of musical contents.

Next, at Step S6, the physiological data measurer 102 determines whether the output of the musical content has been completed. At this point, when it is determined that the output of the musical content has not been completed (NO at Step S6), the processing returns to Step S5, and the musical content outputter 101 continuously outputs the musical content to the outside. It is to be noted that when a plurality of musical contents are output, at Step S6, the physiological data measurer 102 may determine whether the output of one musical content out of the plurality of musical contents has been completed.

By contrast, when it is determined that the output of the musical content has been completed (YES at Step S6), at Step S7, the physiological data measurer 102 determines whether a predetermined period of time has been elapsed after the output of the musical content has been completed. At this point, when it is determined that a predetermined period of time has not been elapsed after the output of the musical content has been completed (NO at Step S7), the processing of Step S7 is repeatedly performed until the predetermined period of time has elapsed.

By contrast, when it is determined that a predetermined period of time has been elapsed after the output of the musical content has been completed (YES at Step S7), at Step S8, the physiological data measurer 102 measures the physiological data of the user. On the physiological data measured at this point, the emotional state of the user changed by listening to the musical content is reflected.

Next, at Step S9, the communicator 105 transmits the physiological data measured by the physiological data measurer 102 to the content providing device 200. It is to be noted that when a plurality of musical contents are output, each time one musical content out of the plurality of musical contents is output, the processing from Step S6 to Step S9 may be performed. Furthermore, while the processing from Step S6 to Step S9 is being performed, the next musical content is to be output. Furthermore, the communicator 105 may transmit the measured physiological data each time each of the plurality of musical contents is output. Alternatively, when all of the plurality of musical contents have been output, the communicator 105 may transmit a plurality of pieces of physiological data measured for each of the plurality of musical contents.

Next, at Step S21, the communicator 201 of the content providing device 200 receives the physiological data transmitted by the terminal device 100. The communicator 201 outputs the received physiological data to the musical content determiner 207, the rhythm feedback reflector 202, and the reaction feedback reflector 204.

Next, at Step S22, the time information acquirer 206 acquires the time information indicating the present time. The time information acquirer 206 outputs the acquired time information to the rhythm feedback reflector 202.

Next, at Step S23, the rhythm feedback reflector 202 calculates the present emotional state value representing the present emotional state of the user based on the physiological data and generates the rhythm characteristic data associating the present time acquired by the time information acquirer 206 and the calculated present emotional state value.

Next, at Step S24, the rhythm feedback reflector 202 stores the generated rhythm characteristic data in the rhythm characteristic data storage 203. It is to be noted that when the rhythm characteristic data in a state in which no musical content is provided to the user is acquired, the processing from Step S22 to Step S24 may not be performed.

Next, at Step S25, the reaction feedback reflector 204 calculates the emotional state change value representing the emotional state of the user changed with the musical content provided based on the physiological data received by the communicator 201 and the musical feature amount extracted by the musical feature amount extractor 209, and generates the response profile data associating the user ID, the tune ID, the tune title, the musical feature amount, and the emotional state change value.

Next, at Step S26, the reaction feedback reflector 204 stores the generated response profile data in the response profile data storage 205.

As described above, the musical content for changing the emotional state is determined in accordance with the difference value between the target emotional state value representing the emotional state targeted by the user and the present emotional state value representing the present emotional state of the user, and the determined musical content is provided to the user, whereby the emotional state of the user can be guided to the emotional state targeted by the user.

The content providing method, the content providing device, and the content providing program according to the present disclosure can guide the emotional state of the user to the emotional state targeted by the user, and are effective as the content providing method, the content providing device, and the content providing program for providing a content for changing the emotional state to the user.

«Supplementation»

A content providing method according to an aspect of the present disclosure includes (A) a step of receiving, from a user device, user ID information for specifying a user, a target emotional state value representing a target emotional state that the user is to reach, and target time information indicating a time when the user is to reach the target emotional state, (B) a step of acquiring personal physiological rhythm data of the user associated with the user ID information from a data storage, the personal physiological rhythm data including a plurality of emotional state values representing emotional states of the user at different times, (C) a step of acquiring present time information indicating a present time, (D) a step of determining one, which corresponds to the present time, selected from the plurality of emotional state values as a present emotional state value representing a present emotional state of the user, (E) a step of calculating a difference value between the present emotional state value and the target emotional state value, (F) a step of estimating, based on the physiological rhythm data, a spontaneous variation by which an emotional state value of the user is assumed to change during a period from the present time to the target time if no content is provided, (G) a step of compensating the difference value by the spontaneous variation, (H) a step of selecting, from among a plurality of contents registered in a content database, at least one content that is expected to cause the emotional state value of the user to change by the compensated difference value, and (I) a step of providing the selected at least one content to the user device.

As examples of the steps (A), (B), (C), and (D), Steps S11, S12, S14, and S15 in FIG. 5 can be cited, respectively. As an example of the steps (E), (F), and (G), Step S16 in FIG. 5 can be cited. As examples of the steps (H) and (I), Steps S17 and S20 in FIG. 5 can be cited.

As an example of the "physiological rhythm data", the "rhythm characteristic data" described in the embodiment can be cited. The physiological rhythm data may be circadian rhythm data indicating a circadian rhythm, for example. As an example of the "spontaneous variation", the "compensated value" described in the embodiment can be cited.

The content providing method according to the above-described aspect solves the technical problem described below with the steps (F) and (G) included, in particular. With the technique according to the present disclosure, a computer selects a content while predicting a future emotional state of the user such that the emotional state of the user reaches a desired state by the target time and provides the selected content. However, the emotional state of the user changes with a factor other than the content (for example, a circadian rhythm), and the degree of the change greatly differs among individuals. In particular, as the period from the present time to the target time becomes long, the accuracy with which the computer predicts the future emotional state of the user tends to be insufficient. As a measure against this, a method is thinkable with which the period from the present time to the target time is separated into a plurality of short times and the emotional state of the user is monitored to eliminate a deviation of the predication each time. Alternatively, another method is thinkable with which more than sufficient contents are provided in advance so that the emotional state of the user can securely exceed a desired state by the target time. However, each of the above-described measures requires an excessive amount of processing to be performed by the user device and the content providing device and/or has a risk of generating an excessive amount of data communication between these devices. Compared with the methods using these measures, with the content providing method according to the above-described aspect, even when the period from the present time to the target time is long, the computer can accurately predict the future emotional state of the user with one prediction process and avoid an excessive amount of data communication. In view of this, the content providing method according to the above-described aspect has a technical advantage.

In the above-described aspect, generating the physiological rhythm data may be performed by continuously or intermittently performing a cycle including the following (b1) to (b3) plural times during a predetermined period, (b1) a step of acquiring physiological data of the user through at least one sensor, (b2) a step of acquiring acquisition time information indicating an acquisition time when the physiological data are acquired, and (b3) a step of calculating the emotional state value of the user at the acquisition time, based on the physiological data and the acquisition time information.

As examples of the steps (b1), (b2), and (b3), Steps S21, S22, and S23 FIG. 6 can be cited, respectively.

It is to be noted that the "acquisition time" may be the time at which the terminal device has measured the physiological data, or may be the time at which the content providing device has received the physiological data.

In the above-described aspect, each of the plurality of contents may be, in a reaction characteristic database, associated with a reactive variation by which the emotional state value of the user is assumed to change due to the each of the plurality of contents.

As an example of the "reactive variation" in the present disclosure, the "emotional state change value" in the embodiment can be cited.

Furthermore, the above-described step (H) may include (h1) a substep of selecting, from among a plurality of reactive variations registered in the reaction characteristic database, a combination of reactive variations corresponding to the compensated difference value, and (h2) a substep of determining the at least one content associated with the selected combination of the reactive variations.

The "combination of the reactive variations" according to the present disclosure may be a single reactive variation, may be the total obtained by adding several times the same reactive variation, or may be the total obtained by adding a plurality of reactive variations different from one another.

The reactive variation corresponding to each content may be calculated based on the physiological data that has been actually measured, or may be estimated from a known reactive variation based on similarity in the feature amounts of the plurality of contents.

In the former case, the following steps (i) to (vi) may be performed for each of contents, (i) a step of acquiring first physiological data of the user through at least one sensor, (ii) a step of causing the user device to play a content for the user after the step of (i), (iii) a step of acquiring second physiological data of the user through the at least one sensor after the step of (ii), (iv) a step of calculating a first emotional state value of the user, based on the first physiological data, (v) a step of calculating a second emotional state value of the user, based on the second physiological data, and (vi) a step of associating a variation between the first emotional state value and the second emotional state value as the reactive variation with the played content.

The above-described steps (i) to (vi) are implemented by combining Steps S20, S21, S23, and S24 in the present embodiment, for example.

In the latter case, the following steps (α) to (γ) may be performed, (α) a step of extracting a plurality of feature amounts from the plurality of contents and registering the plurality of feature amounts into the reaction characteristic database, (β) a step of estimating the plurality of reactive variations based on the plurality of feature amounts, and (γ) a step of registering, into the reaction characteristic database, the plurality of reactive variations in association with the plurality of feature amounts.

What is claimed is:

1. A computer-implemented method for selectively providing content, the method comprising:
    receiving, from a user device, a user ID for specifying a user, a target emotional state value representing a target emotional state that the user reaches, and a target time indicating a time when the user reaches the target emotional state;
    acquiring personal physiological rhythm data of the user associated with the user ID from a data storage, the personal physiological rhythm data including a plurality of emotional state values representing emotional states of the user at different times;
    acquiring a present time;
    determining a present emotional state value representing a present emotional state of the user, the present emotional state value being an emotional state value selected from the plurality of emotional state values and associated with the present time;
    calculating a difference value between the present emotional state value and the target emotional state value;
    estimating, based on the personal physiological rhythm data of the user, a spontaneous variation indicating a change in an emotional state value of the user during a period from the present time to the target time without providing a content;
    compensating the difference value by the spontaneous variation;
    selecting, from a plurality of contents registered in a content database, at least one content that causes the emotional state value of the user to change by the compensated difference value; and
    providing the selected at least one content to the user device.

2. The method according to claim 1, further comprising:
generating the personal physiological rhythm data of the user by continuously or intermittently performing a cycle including following (A) to (C) a plurality of times during a predetermined period,
    (A) acquiring physiological data of the user through at least one sensor,
    (B) acquiring an acquisition time when the physiological data are acquired, and
    (C) calculating the emotional state value of the user at the acquisition time, based on the physiological data and the acquisition time.

3. The method according to claim 2, wherein
the physiological data includes at least one of blood flow, heart rate, pulse rate, brain wave, or blood pressure of the user.

4. The method according to claim 1, wherein
each of the plurality of contents is, in a reaction characteristic database, associated with a reactive variation by which the emotional state value of the user changes due to the each of the plurality of contents, and
the selecting of the at least one content includes:
    selecting, from a plurality of reactive variations registered in the reaction characteristic database, a combination of at least one reactive variation corresponding to the compensated difference value, and
    determining the at least one content associated with the selected combination of the at least one reactive variation.

5. The method according to claim 4, further comprising:
registering, into the reaction characteristic database, the plurality of reactive variations in association with the plurality of contents by performing the following (A) to (F) for each of the plurality of contents,
    (A) acquiring first physiological data of the user through at least one sensor,
    (B) causing the user device to play a content for the user after (A),
    (C) acquiring second physiological data of the user through the at least one sensor after (B),
    (D) calculating a first emotional state value of the user, based on the first physiological data,
    (E) calculating a second emotional state value of the user, based on the second physiological data, and
    (F) associating a variation between the first emotional state value and the second emotional state value as the reactive variation with the played content.

6. The method according to claim 4, further comprising:
extracting a plurality of features from the plurality of contents; and
registering the plurality of features into the reaction characteristic database.

7. The method according to claim 6, further comprising:
estimating the plurality of reactive variations based on the plurality of features; and
registering, into the reaction characteristic database, the plurality of reactive variations in association with the plurality of features.

8. The method according to claim 1, wherein
the personal physiological rhythm data of the user is circadian rhythm data indicating a circadian rhythm of the user.

9. The method according to claim 1, wherein
the content includes a music content.

10. The method according to claim 1, wherein
each of the target emotional state value and the plurality of emotional state values are coordinate values in two-dimensional coordinates with arousal degree and emotional valence being coordinate axes.

11. A device comprising:
a memory that stores a program; and
a processor, when executing the program stored in the memory, that performs operations including:
receiving, from a user device, a user ID for specifying a user, a target emotional state value representing a target emotional state that the user reaches, and a target time indicating a time when the user reaches the target emotional state;
acquiring personal physiological rhythm data of the user associated with the user ID from a data storage, the personal physiological rhythm data including a plurality of emotional state values representing emotional states of the user at different times;
acquiring a present time;
determining a present emotional state value representing a present emotional state of the user, the present emotional state value being an emotional state value selected from the plurality of emotional state values and associated with the present time;
calculating a difference value between the present emotional state value and the target emotional state value;
estimating, based on the personal physiological rhythm data of the user, a spontaneous variation indicating a change in an emotional state value of the user during a period from the present time to the target time without providing a content;
compensating the difference value by the spontaneous variation;
selecting, from a plurality of contents registered in a content database, at least one content that causes the emotional state value of the user to change by the compensated difference value; and
providing the selected at least one content to the user device.

12. A non-transitory recording medium that stores a program causing a computer to perform operations comprising:
receiving, from a user device, a user ID for specifying a user, a target emotional state value representing a target emotional state that the user reaches, and a target time indicating a time when the user reaches the target emotional state;
acquiring personal physiological rhythm data of the user associated with the user ID from a data storage, the personal physiological rhythm data including a plurality of emotional state values representing emotional states of the user at different times;
acquiring a present time;
determining a present emotional state value representing a present emotional state of the user, the present emotional state value being an emotional state value selected from the plurality of emotional state values and associated with the present time;
calculating a difference value between the present emotional state value and the target emotional state value;
estimating, based on the personal physiological rhythm data of the user, a spontaneous variation indicating a change in an emotional state value of the user during a period from the present time to the target time without providing a content;
compensating the difference value by the spontaneous variation;
selecting, from a plurality of contents registered in a content database, at least one content that causes the emotional state value of the user to change by the compensated difference value; and
providing the selected at least one content to the user device.

* * * * *